(12) United States Patent
Berkner et al.

(10) Patent No.: US 7,157,589 B2
(45) Date of Patent: Jan. 2, 2007

(54) ONE STEP PROCESS FOR THE PREPARATION OF ANTICONVULSANT DERIVATIVES

(75) Inventors: Joachim Ernst Berkner, Suwanee, GA (US); Scott Duncan, Madison, WI (US); John Mills, Hatfield, PA (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 68 days.

(21) Appl. No.: 10/790,274

(22) Filed: Mar. 1, 2004

(65) Prior Publication Data

US 2004/0215004 A1 Oct. 28, 2004

Related U.S. Application Data

(60) Provisional application No. 60/451,863, filed on Mar. 4, 2003.

(51) Int. Cl.
*C07D 493/00* (2006.01)
*C07C 305/00* (2006.01)

(52) U.S. Cl. ............... 549/336; 549/337; 549/387; 549/396; 549/426; 549/427; 549/433; 549/443; 558/48; 564/89; 564/90

(58) Field of Classification Search ........... 549/387, 549/336, 337, 396, 476, 427, 433, 443; 558/48; 564/89, 90
See application file for complete search history.

(56) References Cited

U.S. PATENT DOCUMENTS 4,513,006 A 4/1985 Maryanoff et al.
4,582,916 A 4/1986 Gardocki et al.
5,387,700 A 2/1995 Maryanoff et al.

OTHER PUBLICATIONS

Hatt et al., Aust. Jol. Chem. vol. 18, No. 123 pp. 2045-2048(1965) Chem Abstract best availible copy.*
Vatele, J-M et al., "Design and Reactivity of Organic Functional Groups—Preparation and Nucleophilic Displacement Reactions fo Imimdazole-1-Sulfonates (Imidazylates)", Tetrahedron, Elsevier Science Publishers, Amsterdam, Netherlands, vol. 52, No. 32, 1996, pp. 10557-10568.
PCT International Search Report, dated Aug. 3, 2004, for PCT Int'l. Appln. No. PCR/US2004/006263.

* cited by examiner

*Primary Examiner*—Cecilia J. Tsang
*Assistant Examiner*—Raymond Covington
(74) *Attorney, Agent, or Firm*—Mary A. Appollina

(57) ABSTRACT

The present invention is directed to a one-step process for the preparation of fructopyranose sulfamate derivatives of the general formula (I)

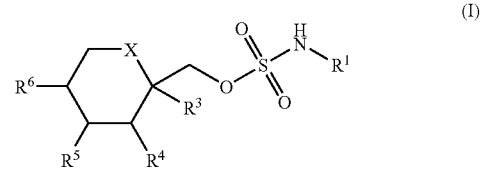

wherein X, $R^1$, $R^3$, $R^4$, $R^5$ and $R^6$ are as described in the specification.

29 Claims, No Drawings

ONE STEP PROCESS FOR THE PREPARATION OF ANTICONVULSANT DERIVATIVES

CROSS REFERENCE TO RELATED APPLICATION

This application claims priority from U.S. provisional application Ser. No. 60/451,863, filed on Mar. 4, 2003, the contents of which are hereby incorporated by reference.

FIELD OF THE INVENTION

The present invention relates to a one step process for the preparation of compounds of the formula (I)

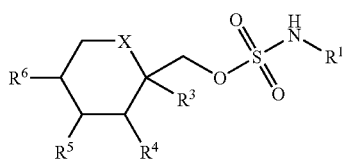

(I)

wherein X, $R^1$, $R^3$, $R^4$, $R^5$ and $R^6$ are as hereinafter defined. The compounds of formula (I) are useful for the treatment of epilepsy.

BACKGROUND OF THE INVENTION

The compounds of formula (I)

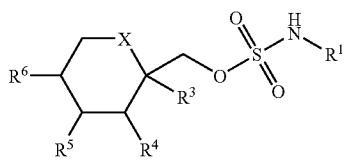

(I)

wherein $R^1$ is selected from the group consisting of hydrogen and $C_{1-4}$alkyl and wherein X, $R^3$, $R^4$, $R^5$ and $R^6$ are as hereinafter defined, are known compounds that have been found to exhibit anticonvulsant activity and are therefore useful in the treatment of conditions such as epilepsy. These compounds are disclosed in U.S. Pat. No. 4,582,916 and U.S. Pat. No. 4,513,006, which also disclose processes for the preparation of said compounds; and which are hereby incorporated by reference.

One process disclosed in the above referenced patents is a process for the preparation of the compounds of formula (I) comprising reacting an alcohol of the formula $RCH_2OH$ with a chlorosulfamate of the formula $ClSO_2NH_2$ or $ClSO_2NHR^1$ in the presence of a base such as potassium t-butoxide or sodium hydride at a temperature of about −20° C. to 25° C. and in a solvent such as toluene, tetrahydrofuran or dimethylformamide, where R is a moiety of the formula (II)

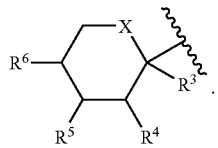

(II)

This process has two major disadvantages. One disadvantage is that the process calls for a combination of NaH and DMF which has an uncontrollable exotherm and is therefore potentially explosive. See J. Buckley et al., Chemical & Engineering News, Jul. 12, 1982, page 5; and G. DeWail, Chemical & Engineering News, Sep. 13, 1982. Another disadvantage is that the process also uses highly toxic and corrosive chlorosulfonyl isocyanate (CSI) to prepare the commercially unavailable sulfamyl chloride ($ClSO_2NH_2$). The CSI is not only difficult to work with, because of its toxicity and corrosiveness, but also is available from only limited suppliers.

Another process for the preparation of compound of formula (I) disclosed in the above mentioned U.S. Pat. No. 4,513,006 comprises reacting an alcohol of the formula $RCH_2OH$ with sulfuryl chloride of the formula $SO_2Cl_2$ in the presence of a base such as triethylamine or pyridine at a temperature of about −40° C. to 25° C. in a diethyl ether or methylene chloride solvent to produce a chlorosulfate of the formula $RCH_2OSO_2Cl_2$. The chlorosulfate of the formula $RCH_2OSO_2Cl_2$ may then be reacted with an amine of the formula $R^1NH_2$ at a temperature of about −40° C. to 25° C. in a methylene chloride or acetonitrile solvent to produce the compound of formula (I). This process utilizing diethyl ether, methylene chloride and acetonitrile solvents produces relatively low yields of the desired end product of formula (I).

A third process disclosed in the two patents mentioned above comprises reacting the chlorosulfate of formula $RCH_2OSO_2Cl_2$ formed as previously described with a metal azide such as sodium azide in a solvent such as methylene chloride or acetonitrile to yield an azidosulfate of the formula $RCH_2OSO_3N_3$. The azidosulfate is then reduced to the compound of formula I wherein $R^1$ is hydrogen, by catalytic hydrogenation.

The disadvantage with this process is that explosions may occur when handling the azide compounds. Also, the process contains an additional chemical transformation involving the reduction of the azide to the $NH_2$ moiety.

Maryanoff et al. in U.S. Pat. No. 5,387,700 disclose a process for the preparation of compounds of formula (I) which comprises reacting an alcohol of the formula $RCH_2OH$ with sulfuryl chloride in the presence of a base, in a solvent selected from the group consisting of toluene, t-butyl methyl ether and tetrahydrofuran, to form a chlorosulfate intermediate of the formula $RCH_2OSO_2Cl_2$. The chlorosulfate of formula $RCH_2OSO_2Cl_2$ is reacted with an amine of the formula $R_1NH_2$, in a solvent selected from the group consisting of tetrahydrofuran, t-butyl methyl ether and lower alkanol (e.g. methanol or ethanol) to form the compound of formula (I).

One disadvantage of this process is that the compound of formula (I) is prepared in a batch process wherein the first reaction is carried out, the solvent is removed, the product is isolated, the isolated product is re-dissolved in a second solvent and then reacted to form the final product. This results in a process which requires isolation of a semi-stable, thermally labile ROSO$_2$Cl intermediate. Additionally, this process requires handling of multiple solvents and multiple solvent recovery processes for recycling or disposal resulting in a process which is both cost and labor intensive.

It is an object of the present invention to provide a one step process for the preparation of the compounds of formula (I), a process which uses readily available materials, can be carried out without isolation of intermediates and/or produces relative high yields, thereby allowing for commercial production of the compounds of formula (I).

SUMMARY OF THE INVENTION

The present invention is directed to a one-step process for the preparation of the compounds of formula (I)

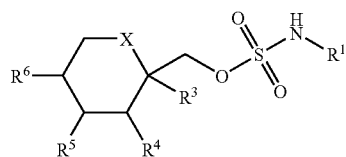

(I)

wherein

X is selected from CH$_2$ or O;

R$^1$ is selected from the group consisting of hydrogen and C$_{1-4}$alkyl;

R$^3$, R$^4$, R$^5$ and R$^6$ are each independently selected from hydrogen or lower alkyl and, when X is CH$_2$, R$^5$ and R$^6$ may be alkene groups joined to form a benzene ring and, when X is O, R$^3$ and R$^4$ and/or R$^5$ and R$^6$ together may be a methylenedioxy group of the formula:

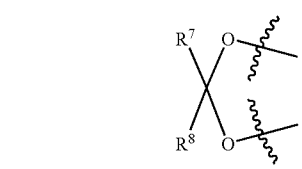

wherein

R$^7$ and R$^8$ are same or different and are hydrogen, lower alkyl or are alkyl and are joined to form a cyclopentyl or cyclohexyl ring;

comprising

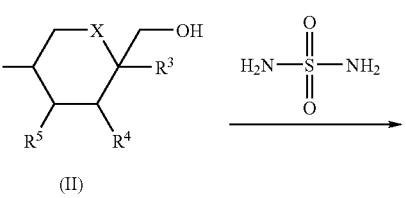

(II)

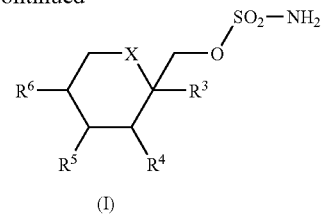

(I)

reacting a compound of formula (II) with sulfuryl diamide (also known as sulfamide), at an elevated temperature, in the presence of from 0 to about 10% water, to yield the corresponding compound of formula (I).

The present invention is further directed to a process for the preparation of a compound of formula (Ia),

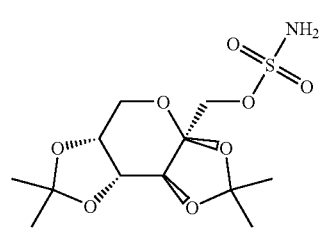

(Ia)

also known as topiramate, comprising

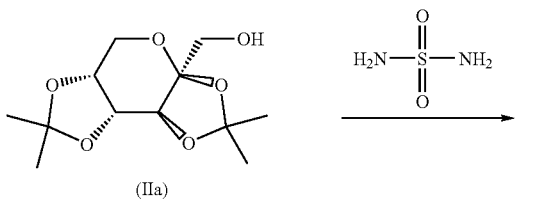

(IIa)

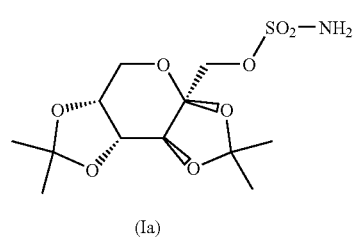

(Ia)

reacting a compound of formula (IIa) (also known as diacetone fructose or DAF) with sulfuryl diamide (also known as sulfamide), at an elevated temperature, in the presence of from 0 to about 10% water, to yield the corresponding compound of formula (Ia).

The present invention is further directed to a compound prepared according to any of the processes described herein.

Illustrative of the invention is a pharmaceutical composition comprising a pharmaceutically acceptable carrier and a compound prepared according to any of the processes described above.

An illustration of the invention is a pharmaceutical composition made by mixing a pharmaceutically acceptable carrier and a compound prepared according to any of the processes described above.

Illustrating the invention is a process for making a pharmaceutical composition comprising mixing a pharmaceutically acceptable carrier and a compound prepared according to the processes described above.

Another example of the invention is the use of a compound prepared according to any of the processes described herein in the preparation of a medicament for treating epilepsy.

DETAILED DESCRIPTION OF THE INVENTION

In an embodiment of the present invention, the compound of formula (I) is topiramate, a compound of the formula (Ia)

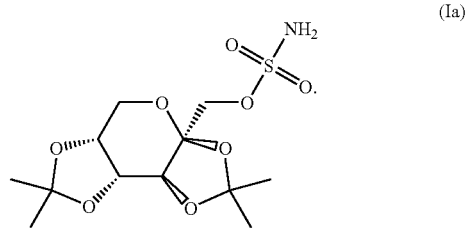

(Ia)

As used herein, the terms "diacetone fructose" and "DAF" shall mean diacetone-β-D-fructose, a compound of formula (IIa)

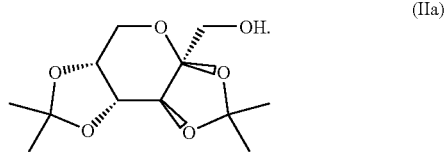

(IIa)

As used herein, the term "alkyl", whether used alone or as part of a substituent group, shall include straight and branched carbon chains. For example, alkyl groups include methyl, ethyl, propyl, isopropyl, butyl, isopbutyl, sec-butyl, tert-butyl, pentyl, and the like. Unless otherwise noted, the term "lower" when used with alkyl shall mean carbon chain compositions of one to four carbon atoms.

As used herein, the notation "*" shall denote the presence of a stereogenic center.

As used herein, the term "elevated temperature" shall mean a temperature greater than about 90° C., preferably a temperature greater than or equal to the reflux temperature of the solvent of the reaction mixture, more preferably a temperature in the range of about 90° C. to about 170° C., more preferably still at a temperature in the range of about 110° C. to about 160° C., more preferably still at a temperature in the range of about 120° C. to about 140° C.

As used herein, unless otherwise noted, the term "in the presence of from 0 to about 10% water" shall mean that the total molar amount of water relative to the molar amount of DAF is in the range of from 0 to about 10%.

As used herein, the term "aprotic organic solvent" shall mean any organic solvent that does not yield a proton under the reaction conditions. Suitable examples include, but are not limited to, xylene (for example o-xylene, p-xylene, m-xylene or a mixture thereof), ethyl benzene, mesitylene, tetrahydronaphthalene, pyridine, 1-methyl-2-pyrrolidinone, toluene, 4-methyl-2-pentanone, benzonitrile, dimethylformamide, sulfolane, diphenyl ether, and the like.

The term "subject" as used herein, refers to an animal, preferably a mammal, more preferably a human, who is or has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

One skilled in the art will recognize that the compounds of formula (I) have several stereogenic centers as denoted by the asterisks below.

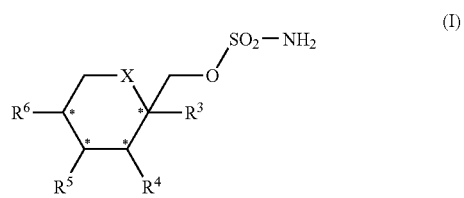

(I)

One skilled in the art will further recognize that the processes of the present invention may be used to prepare racemic mixtures of a compound of the formula (I) or any of the stereoisomers of a compound of formula (I), by selection and substitution of appropriate racemic mixtures or stereoisomers of the reagents.

The present invention is directed to a one step process for the preparation of a compound of formula (I) as outlined in Scheme 1.

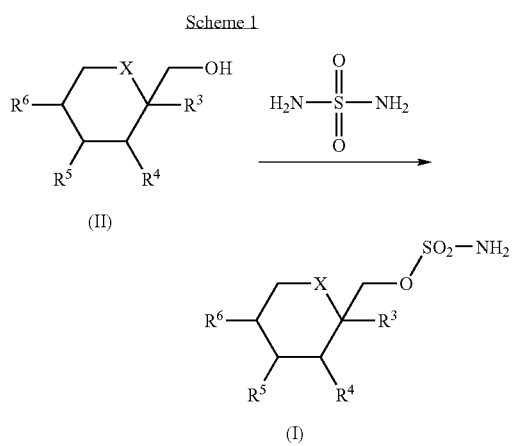

Scheme 1

Accordingly, a suitably substituted compound of formula (II), a known compound or compound prepared by known methods, is reacted with sulfuryl diamide (also known as sulfamide), wherein the sulfuryl diamide is preferably present in an amount greater than or equal to about 0.9 equivalents; more preferably in an amount in the range of about 1.5 to about 3 equivalents; more preferably still in an amount equal to about 2 equivalents;

preferably in the presence of a non-aqueous organic base such as an organic tertiary amine such as pyridine, 4-picoline, isoquinoline, dimethylbutylamine, 4-dimethylaminopyridine, 4-t-butylpyridine, imidazole, tributylamine, dimethylbenzylamine, and the like; or a non-aqueous inorganic base such as $K_2CO_3$, $KHCO_3$, $Na_2CO_3$, $NaHCO_3$, and the like; more preferably, in the presence of a non-aqueous organic tertiary amine; more preferably still, in the presence of pyridine;

wherein the non-aqueous organic or inorganic base is preferably present in an amount greater than about 1 equivalent; more preferably, in an amount in the range of about 3 to about 6 equivalents; more preferably still, in an amount equal to about 4 equivalents;

in the presence of from 0% to about 10% water, preferably from 0% to about 5% water, more preferably from 0% to about 3% water;

preferably in an aprotic organic solvent such as xylene (for example o-xylene, p-xylene, m-xylene or a mixture thereof), ethyl benzene, mesitylene, tetrahydronaphthalene, pyridine, 1-methyl-2-pyrrolidinone, toluene, 4-methyl-2-pentanone, benzonitrile, dimethylformamide, sulfolane, diphenyl ether, and the like; or a mixture of aprotic organic solvents such as diphenyl ether:biphenyl, xylene:toluene, technical grade mixed xylenes, and the like; more preferably in o-xylene, p-xylene, m-xylene, a mixture thereof or a technical grade mixed xylenes;

alternatively, the solvent may be selected from a non-aqueous organic base such as an organic tertiary amine, for example, pyridine, 4-picoline, isoquinoline, dimethylbutylamine, 4-dimethylaminopyridine, 4-t-butylpyridine, imidazole, tributylamine, dimethylbenzylamine, and the like; preferably, a non-aqueous organic tertiary amine; more preferably, pyridine;

alternatively still, when the compound of formula (II) is reacted in the presence of a non-aqueous organic base, the non-aqueous organic base may act as the solvent;

at an elevated temperature, preferably at a temperature in the range of from about 90° C. to about 170° C.; more preferably, at a temperature in the range of from about 110° C. to about 160° C.; more preferably still at a temperature in the range of from about 120° C. to about 140° C.;

to yield the corresponding compound of formula (I).

Preferably, the compound of formula (II) is reacted with sulfuryl diamide, according to the process outlined in Scheme 1 above, in the absence of any other alcohol (i.e. an alcohol other than the compound of formula (II)).

The compound of formula (Ia) may be prepared according to the process outlined in Scheme 2.

Scheme 2

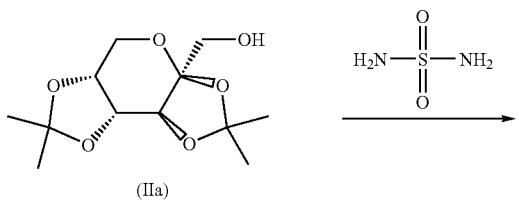

(IIa)

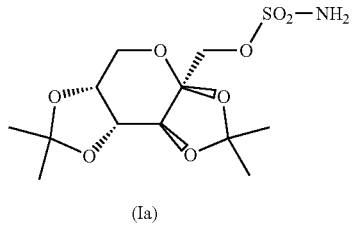

(Ia)

Accordingly, a compound of formula (IIa), a known compound also known as diacetone fructose (DAF), is reacted with sulfuryl diamide (also known as sulfamide), wherein the sulfuryl diamide is preferably present in an amount greater than or equal to about 0.9 equivalents; more preferably in an amount in the range of about 1.5 to about 3 equivalents; more preferably still in an amount equal to about 2 equivalents;

preferably in the presence of a non-aqueous organic base such as an organic tertiary amine such as pyridine, 4-picoline, isoquinoline, dimethylbutylamine, 4-dimethylaminopyridine, 4-t-butylpyridine, imidazole, tributylamine, dimethylbenzylamine, and the like; or a non-aqueous inorganic base such as $K_2CO_3$, $KHCO_3$, $Na_2CO_3$, $NaHCO_3$, and the like; more preferably, in the presence of a non-aqueous organic tertiary amine; more preferably still, in the presence of pyridine;

wherein the non-aqueous organic or inorganic base is preferably present in an amount greater than about 1 equivalent; more preferably, in an amount in the range of about 3 to about 6 equivalents; more preferably still, in an amount equal to about 4 equivalents;

in the presence of from 0% to about 10% water, preferably from 0% to about 5% water, more preferably from 0% to about 3% water;

preferably in an aprotic organic solvent such as xylene (for example o-xylene, p-xylene, m-xylene or a mixture thereof), ethyl benzene, mesitylene, tetrahydronaphthalene, pyridine, 1-methyl-2-pyrrolidinone, toluene, 4-methyl-2-pentanone, benzonitrile, dimethylformamide, sulfolane, diphenyl ether, and the like; or a mixture of aprotic organic solvents such as diphenyl ether:biphenyl, xylene:toluene, technical grade mixed xylenes, and the like; more preferably in o-xylene, p-xylene, m-xylene, a mixture thereof or a technical grade mixed xylenes;

alternatively, the solvent may be selected from a non-aqueous organic base such as an organic tertiary amine, for example, pyridine, 4-picoline, isoquinoline, dimethylbutylamine, 4-dimethylaminopyridine, 4-t-butylpyridine, imidazole, tributylamine, dimethylbenzylamine, and the like; preferably, a non-aqueous organic tertiary amine; more preferably, pyridine;

alternatively still, when the compound of formula (II) is reacted in the presence of a non-aqueous organic base, the non-aqueous organic base may act as the solvent;

at an elevated temperature, preferably at a temperature in the range of from about 90° C. to about 170° C.; more preferably, at a temperature in the range of from about 110° C. to about 160° C.; more preferably still at a temperature in the range of from about 120° C. to about 140° C.;

to yield the corresponding compound of formula (Ia).

Preferably, the compound of formula (IIa) is reacted with sulfuryl diamide, according to the process outlined in Scheme 2 above, in the absence of any other alcohol (i.e. an alcohol other than the compound of formula (IIa)).

Where the compounds of the present invention have at least one chiral (or stereogenic) center, they may accordingly exist as enantiomers. Where the compounds possess two or more chiral (or stereogenic) centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

Where the processes for the preparation of the compounds according to the invention give rise to a mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The following examples describe the invention in greater detail and are intended to illustrate the invention, but not to limit it.

EXAMPLE A1

Experimental Runs #101–116:

A reactor was charged with DAF, sulfamide, base, and solvent, as described in Table 1. While agitating, the reaction mixture was heated and held at the desired temperature and for the selected amount of time (as listed in Table 2).

For experimental runs 101, 102, 103, the mixture was distilled at 41° C., under vacuum, for 30, 35 and 20 minutes, respectively.

The reaction mixtures were cooled to room temperature, then extracted twice with about 50 mL of a 1M aqueous NaOH solution (An 0.3 M solution of aqueous NaOH was used for experimental runs #101–108). The resulting basic product solution was neutralized using 6M aqueous HCl solution. After crystallization, the product solution was filtered, and the wet cake was dried for between 16–20 hours (about 22 hours for experimental runs # 106 and 107) at about 50° C. under vacuum to yield topiramate product. The dry product was analyzed by HPLC.

Experimental Runs # 117–139:

A reactor was charged with DAF, sulfamide, base, and solvent, as described in Table 1. While agitating, the reaction mixture was heated and held for a period of about 60 minutes at the desired temperature (as listed in Table 2). After cooling to room temperature, the reaction mixture was extracted twice with about 75 mL of 1M aqueous NaOH solution. The resulting basic product solution was neutralized using 6M aqueous HCl solution. After crystallization, the product solution was filtered, and the wet cake was dried for 16–20 hours (~24 hours for experimental runs 129, 134, 137 and ~48 hours for experimental runs # 126, 128, 130, 131, 136) at about 50° C. vacuum to yield topiramate product. Experimental runs # 123, 125 and 135 were expected to yield product, but were abandoned due to difficulties during extraction or crystallization. The dry product was analyzed by HPLC.

The above described procedures were completed according to the run conditions as listed in Table 1 and 2 below. Topiramate product was produced in all experimental runs except as noted above.

TABLE 1

| Run # | DAF | Sulfamide | Base | Base | Solvent |
|---|---|---|---|---|---|
| 101 | 10.05 g<br>38.62 mmol | 7.43 g<br>77.32 mmol | pyridine | 12.14 g<br>153.48 mmol | mixed xylenes<br>100 mL |
| 102 | 10.0 g<br>38.43 mmol | 7.39 g<br>76.9 mmol | pyridine | 12.16 g<br>153.73 mmol | mixed xylenes<br>100 mL |
| 103 | 10.0 g<br>38.43 mmol | 7.33 g<br>76.27 mmol | pyridine | 12.18 g<br>153.98 mmol | mixed xylenes<br>100 mL |
| 104 | 10.0 g<br>38.43 mmol | 7.43 g<br>77.32 mmol | pyridine | 12.34 g<br>156.01 mol | mixed xylenes<br>100 mL |
| 105 | 10.01 g<br>38.47 mmol | 7.39 g<br>76.9 mmol | pyridine | 12.17 g<br>153.86 mmol | mixed xylenes<br>101 mL |
| 106 | 10.01 g<br>38.47 mmol | 7.39 g<br>76.9 mmol | pyridine | 12.45 g<br>157.4 mmol | mixed xylenes<br>101 mL |
| 107 | 10.01 g<br>38.47 mmol | 7.44 g<br>77.42 mmol | pyridine | 12.15 g<br>153.6 mmol | mixed xylenes<br>51 mL |
| 108 | 10.02 g<br>38.50 mmol | 7.38 g<br>76.8 mmol | 4-picoline | 12.54 g<br>134.65 mmol | mesitylene<br>50 mL |
| 109 | 14.98 g<br>57.56 mmol | 11.08 g<br>115.3 mmol | pyridine | 18.33 g<br>231.73 mmol | mixed xylenes<br>150 mL |
| 110 | 9.99 g<br>38.39 mmol | 7.39 g<br>76.9 mmol | Pyridine | 12.14 g<br>153.48 mmol | O-xylene<br>99 mL |

TABLE 1-continued

| Run # | DAF | | Sulfamide | | Base | Base | | Solvent |
|---|---|---|---|---|---|---|---|---|
| 111 | 10.04 | g | 7.31 | g | Pyridine | 12.14 | g | O-xylene |
|  | 38.58 | mmol | 76.07 | mmol |  | 153.48 | mmol | 100 mL |
| 112 | 10.03 | g | 7.39 | g | Pyridine | 12.22 | g | O-xylene |
|  | 38.54 | mmol | 76.9 | mmol |  | 154.49 | mmol | 100 mL |
| 113 | 10.02 | g | 7.39 | g | Pyridine | 12.22 | g | O-xylene |
|  | 38.50 | mmol | 76.9 | mmol |  | 154.49 | mmol | 100 mL |
| 114 | 9.98 | g | 7.38 | g | Pyridine | 12.25 | g | O-xylene |
|  | 38.35 | mmol | 76.8 | mmol |  | 154.87 | mmol | 100 mL |
| 115 | 10.02 | g | 7.36 | g | pyridine | 12.4 | g | O-xylene |
|  | 38.5 | mmol | 76.59 | mmol |  | 156.76 | mmol | 99 mL |
| 116 | 10.0 | g | 7.36 | g | Pyridine | 12.16 | g | O-xylene |
|  | 38.43 | mmol | 76.59 | mmol |  | 153.73 | mmol | 100 mL |
| 117 | 29.92 | g | 22.31 | g | Pyridine | 36.52 | g | O-xylene |
|  | 114.98 | mmol | 232.15 | mmol |  | 461.49 | mmol | 302 mL |
| 118 | 30.06 | g | 22.3 | g | Pyridine | 36.68 | g | O-xylene |
|  | 115.51 | mmol | 232.05 | mmol |  | 463.72 | mmol | 150 mL |
| 119 | 30.07 | g | 22.34 | g | 4-picoline | 42.48 | g | 1:1 O-xylene:4-picoline |
|  | 115.55 | mmol | 232.47 | mmol |  | 456.14 | mmol | 150 mL |
| 120 | 30.03 | g | 22.22 | g | Pyridine | 36.58 | g | O-xylene |
|  | 115.4 | mmol | 231.22 | mmol |  | 462.45 | mmol | 75 mL |
| 121 | 30.04 | g | 22.23 | g | Pyridine | 36.55 | g | O-xylene |
|  | 115.44 | mmol | 231.32 | mmol |  | 462.07 | mmol | 40.0 mL |
| 122 | 29.98 | g | 22.18 | g | pyridine | 36.37 | g | none |
|  | 115.09 | mmol | 230.8 | mmol |  | 459.8 | mmol |  |
| 123 | 30.02 | g | 22.34 | g | 4-picoline | 42.91 | g | none |
|  | 115.36 | mmol | 232.47 | mmol |  | 460.75 | mmol |  |
| 124 | 30.09 | g | 22.24 | g | iso-quinoline | 58.11 | g | none |
|  | 115.63 | mmol | 231.43 | mmol |  | 449.91 | mmol |  |
| 125 | 30.01 | g | 22.18 | g | 4-picoline | 42.92 | g | tetrahydro-naphthalene |
|  | 115.32 | mmol | 230.8 | mmol |  | 460.86 | mmol | 40 mL |
| 126 | 30.01 | g | 22.17 | g | 4-picoline | 42.8 | g | tetrahydro-naphthalene |
|  | 115.32 | mmol | 230.7 | mmol |  | 459.57 | mmol | 41 mL |
| 127 | 29.99 | g | 22.34 | g | dimethy-butyl-amine | 59.95 | g | tetrahydro-naphthalene |
|  | 115.24 | mmol | 232.47 | mmol |  | 757.9 | mmol | 40 mL |
| 128 | 30.02 | g | 22.22 | g | pyridine | 36.56 | g | tetrahydro-naphthalene |
|  | 115.36 | mmol | 231.22 | mmol |  | 462.2 | mmol | 40 mL |
| 129 | 29.95 | g | 22.32 | g | pyridine | 36.45 | g | diphenyl ether |
|  | 115.09 | mmol | 232.26 | mmol |  | 460.81 | mmol | 41 mL |
| 130 | 30.02 | g | 22.34 | g | 4-picoline | 43.03 | g | diphenyl ether |
|  | 115.36 | mmol | 232.47 | mmol |  | 462.04 | mmol | 40.5 mL |
| 131 | 29.99 | g | 22.24 | g | 4-picoline | 42.94 | g | O-xylene |
|  | 115.24 | mmol | 231.43 | mmol |  | 461.08 | mmol | 40 mL |
| 132 | 30.03 | g | 22.5 | g | pyridine | 36.12 | g | O-xylene |
|  | 115.4 | mmol | 234.31 | mmol |  | 456.64 | mmol | 40 mL |
| 133 | 10.04 | g | 7.38 | g | iso-quinoline | 20.05 | g | O-xylene |
|  | 38.58 | mmol | 76.8 | mmol |  | 155.23 | mmol | 50 mL |
| 134 | 30.05 | g | 22.21 | g | 4-t-butyl-pyridine | 62.3 | g | O-xylene |
|  | 115.47 | mmol | 231.11 | mmol |  | 460.76 | mmol | 40 mL |
| 135 | 30.08 | g | 22.45 | g | iso-quinoline | 59.65 | g | diphenylether |
|  | 115.59 | mmol | 233.61 | mol |  | 461.83 | mmol | 40.5 mL |
| 136 | 60.08 | g | 44.28 | g | 4-picoline | 85.91 | g | O-xylene |
|  | 230.87 | mmol | 460.77 | mmol |  | 922.47 | mmol | 75 mL |
| 137 | 59.99 | g | 44.44 | g | Pyridine | 73.04 | g | O-xylene |
|  | 230.53 | mmol | 462.43 | mmol |  | 923.39 | mmol | 75 mL |
| 138 | 30.04 | g | 22.5 | g | 4-t-butyl-pyridine | 46.66 | g | O-xylene |
|  | 115.44 | mmol | 234.13 | mmol |  | 345.09 | mmol | 75 mL |
| 139 | 30.02 | g | 22.18 | g | 4-t-butyl-pyridine | 46.68 | g | O-xylene |
|  | 115.36 | mmol | 230.8 | mmol |  | 345.25 | mmol | 75.5 mL |

TABLE 2

| Run # | Time (min) | Temp. (° C.) |
|---|---|---|
| 101 | ~65 | 128–140 |
| 102 | 60 | 135–136 |
| 103 | 65 | 132–136 |
| 104 | 60 | 138–139 |
| 105 | 60 | 134–137 |
| 106 | 65 | 130–136 |
| 107 | 60 | 124–133 |
| 108 | Not available | 130–140 |
| 109 | 80 | 99–114 |
| 110 | 55 | 133–135 |
| 111 | 45 | 130–133 |
| 112 | 50 | 130–134 |
| 113 | 60 | 135–137 |
| 114 | 60 | 134–136 |
| 115 | 62 | 133–137 |
| 116 | 60 | 134–135 |
| 117 | 62 | 135–139 |
| 118 | 60 | 134–136 |
| 119 | 62 | 141–146 |
| 120 | 62 | 130–135 |
| 121 | 60 | 131–133 |
| 122 | 69 | 132–134 |
| 123 | 60 | 150–156 |
| 124 | 62 | 142–144 |
| 125 | 62 | 153–157 |
| 126 | 55 | 130–140 |
| 127 | 60 | 109–112 |
| 128 | 61 | 137–141 |
| 129 | 58 | 139–145 |
| 130 | 67 | 136–140 |
| 131 | 62 | 134–144 |
| 132 | 60 | 130–138 |
| 133 | 60 | 140–135 |
| 134 | 64 | 133–132 |
| 135 | 57 | 130–134 |
| 136 | 64 | 130–138 |
| 137 | 60 | 130–132 |
| 138 | 34 | 130–149 |
| 139 | 41 | 25–120 |

TABLE 3

| | Pyridine Base | | | |
|---|---|---|---|---|
| Run # | DAF | Sulfamide | Base | o-Xylene |
| 140 | 30.01 g | 22.24 g | 36.56 g | 75 mL |
| | 115.32 mmol | 231.43 mmol | 462.2 mmol | |
| 141 | 30.03 g | 22.37 g | 36.78 g | 75.5 mL |
| | 115.4 mmol | 232.78 mmol | 464.98 mmol | |
| 142 | 30.01 g | 22.58 g | 36.5 g | 75.5 mL |
| | 115.32 mmol | 234.96 mmol | 461.44 mmol | |
| 143 | 30.12 g | 22.44 g | 36.68 g | 75 mL |
| | 115.74 mmol | 233.51 mmol | 463.72 mmol | |
| 144 | 30 g | 22.34 g | 36.88 g | 40 mL |
| | 115.28 mmol | 232.47 mmol | 466.25 mmol | |
| 145 | 30.05 g | 22.31 g | 36.51 g | 40 mL |
| | 115.47 mmol | 232.15 mmol | 461.57 mmol | |
| 146 | 30.03 g | 22.24 g | 36.6 g | 40 mL |
| | 115.4 mmol | 231.43 mmol | 462.71 mmol | |
| 147 | 30.07 g | 22.34 g | 36.61 g | 40 mL |
| | 115.55 mmol | 232.47 mmol | 462.83 mmol | |

TABLE 4

| Run # | Time (min) | Temp (° C.) |
|---|---|---|
| 140 | 60 | 130.0–133.4 |
| 141 | 30 | 130.0–132.7 |
| 142 | 60 | 130.0–134.3 |
| 143 | 30 | 130.0–134.7 |
| 144 | 30 | 130.0–130.3 |
| 145 | 60 | 130.0–134.9 |
| 146 | 60 | 130.0–132.8 |
| 147 | 30 | 130.0–133.9 |

EXAMPLE A2

Experimental Runs #140–147; Pyridine Base:

Eight experiments were performed to evaluate combined effects of solvent volume, reaction time, and reaction temperature on one-step synthesis of topiramate, starting with diacetone fructose (DAF).

DAF was combined with sulfamide, pyridine and the chosen volume of o-xylene solvent (in amounts as listed in Table 3) in a 1 liter round-bottomed flask. The charged flask was then submerged in a pre-heated oil bath at the chosen external temperature, and the reaction mixture agitated and heated to the chosen reaction temperature, where it was held for the chosen time before the flask was removed from the oil bath and cooled to room temperature.

The reaction mixture was then extracted twice with 1M NaOH (75 mL portions). The aqueous extracts were combined and neutralized with 6M HCl to induce product crystallization. The product precipitated as an oil in all cases. The oil was agitated overnight to become filterable crystals. The resulting solids were dried under vacuum for 16–18 hrs at 50° C. The dried product was analyzed by HPLC.

Following the above procedure the eight experiments were performed with experimental conditions as listed in Table 3 and 4 below. All experimental runs yielded topiramate product.

EXAMPLE A3

Experimental Runs #148–156: t-Butylpyridine Base:

Nine experiments were performed to evaluate the combined effects of base equivalents, reaction temperature and reaction time on one-step synthesis of topiramate using 4-tert-butylpyridine and starting with diacetone fructose (DAF).

DAF was combined with sulfamide, 4-tert-butylpyridine (in amounts as listed in Table 4) and 40 mL o-xylene in a 500 mL round-bottomed flask. The reaction mixture was agitated and heated to the chosen reaction temperature in an oil bath over about 19–23 min. The reaction mixture was maintained at the chosen reaction temperature for the chosen time, and then cooled rapidly to 25° C. The reaction mixture was extracted twice with 1M NaOH (75 mL portions). The aqueous extracts were combined and neutralized using 6M HCl to induce product crystallization. The product precipitated as an oil in all cases, which was agitated overnight to become filterable crystals. The crystals were dried under vacuum for 16–18 hrs at 50° C. The dried product was analyzed by HPLC.

Following the above procedure the nine experiments were performed with experimental conditions as listed in Table 5 and 6 below. All experimental runs yielded topiramate product.

TABLE 5

4-t-butylpyridine Base

| Run # | DAF | Sulfamide | Base | o-Xylene |
|---|---|---|---|---|
| 148 | 30.16 g<br>115.9 mmol | 22.42 g<br>231.4 mmol | 47.07 g<br>348.1 mmol | 40 mL |
| 149 | 30.20 g<br>116.05 mmol | 22.21 g<br>231.1 mmol | 15.67 g<br>115.9 mmol | 40 mL |
| 150 | 30.12 g<br>115.7 mmol | 22.16 g<br>230.6 mmol | 47.03 g<br>347.8 mmol | 40 mL |
| 151 | 30.23 g<br>116.2 mmol | 22.12 g<br>230.2 mmol | 31.19 g<br>231.7 mmol | 40 mL |
| 152 | 30.10 g<br>115.7 mmol | 22.75 g<br>236.8 mmol | 46.76 g<br>345.8 mmol | 40 mL |
| 153 | 30.03 g<br>115.4 mmol | 22.42 g<br>233.3 mmol | 15.76 g<br>116.6 mmol | 40 mL |
| 154 | 30.23 g<br>116.2 mmol | 22.24 g<br>231.5 mmol | 46.83 g<br>346.4 mol | 40 mL |
| 155 | 30.15 g<br>115.9 mmol | 22.49 g<br>234.1 mmol | 46.85 g<br>346. mmol | 40 mL |
| 156 | 30.08 g<br>115.6 mmol | 22.24 g<br>231.5 mmol | 15.60 g<br>115.4 mmol | 40 mL |

TABLE 6

| Run # | Time (min) | Temp (° C.) |
|---|---|---|
| 148 | 44 | 130.0–150.5 |
| 149 | 60 | 110.0–126.6 |
| 150 | 60 | 110.0–129.0 |
| 151 | 28 | 130.1–146.6 |
| 152 | 29 | 130.0–151.6 |
| 153 | 15 | 130.0–141.5 |
| 154 | 30 | 130.1–143.4 |
| 155 | 15 | 110.1–117.4 |
| 156 | 30 | 110.1–113.7 |

EXAMPLE A4

Multiple experiments were run to evaluate the effect of solvent and base on the one step process for the preparation of topiramate. Experimental conditions were as listed in Tables 7 and 8, with experimental procedures for the individual runs as described below.

Run #157, 158, 160, 164–166:

DAF and sulfamide (in amounts as in Table 8) were transferred to a test tube. The chosen solvent and the chosen base (in amounts as listed in Table 7) were then added to the DAF/sulfamide mixture. The reaction mixture was then agitated and heated, with the reaction mixture maintained at the selected temperature (see Table 8) for the selected time (see Table 8), after which time the upper layer was sampled and analyzed by HPLC.

Run #159,188–198:

DAF, sulfamide, o-xylene and the specified amount of the chosen base (see Tables 7 and 8) were transferred into a 500 mL round-bottomed flask. The reaction mixture was then agitated and heated, with the mixture maintained at the chosen temperature for the chosen time (see Table 8) with an oil bath. The reaction mixture was removed from the hot oil, cooled to about room temperature and then extracted twice with 1M NaOH (75 mL portions). The aqueous extracts were combined and neutralized using 6M HCl to induce product crystallization. The resulting solids were dried under vacuum for 16–18 hrs at 50° C. The dried product was analyzed by HPLC.

Run #161–163

DAF, sulfamide, 4-picoline, and the chosen solvent (in amounts as in Table 7 and 8) were transferred into a 250 mL round-bottomed flask. The flask was lowered into a heated oil bath and the mixture agitated at the selected holding temperature for the selected reaction time (see Table 8). The reaction mixture was then cooled to room temperature and extracted twice with 1M NaOH (75 mL portions). The aqueous extracts were neutralized with 6M HCl and then maintained at room temperature overnight to allow product to crystallize. The resulting crystalline solids were filtered and dried for 16–18 hrs in a vacuum oven at 50° C. The product was then analyzed by HPLC.

Note: Although product was expected in run #162, the product did not crystallize and was therefore not analyzed; the product from run #163 was a sticky solid.

Run #167–172:

The selected solvent in the selected amount (see Table 7) was transferred to a 125 mL test tube along pyridine (in amounts as in Table 7) and the resulting solution heated to the chosen temperature. A pre-weighed mixture of DAF and sulfamide (in amounts as in Table 8) was then added along with transfer washes of solvent (about 2 mL). The reaction mixture was agitated at the chosen temperature for the chosen time (see Table 8) at which time the upper layer was sampled (some mixtures formed a small, dark second layer) and analyzed by HPLC.

Run #173

DAF, sulfamide, pyridine and mixed xylenes (in amounts as listed in Tables 7 and 8) were transferred to a 1000 mL round-bottomed flask in a pre-heated (140° C.) oil bath. The reaction mixture was agitated at the selected reaction temperature for 90 mins. The flask was removed from the oil bath and the residual heat used to distill about 22 g of liquid from the reaction mixture. The reaction mixture was extracted with three portions (90 mL, 30 mL, and 10 mL) of 0.35M NaOH. 1N HCl (50 mL) was added to the aqueous extracts, resulting in the formation of an oil. The mixture was agitated to transform the oil into filterable crystals. The crystals were collected by filtration, washed with water, and dried in a vacuum oven for 16 hrs at 50° C. The product was then analyzed by HPLC analysis.

Run #174–180:

DAF, sulfamide, pyridine and the chosen solvent (in amounts as listed in Tables 7 and 8) were transferred to a 500 ml round-bottomed flask. The reaction mixture was then agitated and heated in an oil bath to the target temperature. The reaction mixture was maintained at about the target temperature (listed in Table 8) for the selected time (see Table 8), removed from the hot oil and cooled to about room temperature. To the reaction mixture was then added water (100 mL) water and/or other solvents (MeOH, 0.5M NaOH, or the reaction solvent) as needed, to achieve a heterogeneous mixture consisting of two clear liquid layers. GC analysis was then performed on both layers.

Run # 181–183

DAF, sulfamide, 4-tert-butylpyridine, and the selected solvent (in amounts as listed in Tables 7 and 8) were transferred to a 500 mL round-bottomed flask. The reaction mixture was then placed in oil bath and agitated while heating at the selected reaction temperature for the selected time (see Table 8). The reaction mixture was then allowed to cool to room temperature. The reaction mixture was then extracted with the appropriate solvents to yield two clear liquid layers (For run 181 the extraction solvents were water (125 mL) and mixed xylenes (25 mL); for run 182 the extraction solvents were water (150 mL) and methanol (25 mL); for run 183 the extraction solvent was 0.3M NaOH (100 mL)). GC analysis was performed on liquid samples from both layers.

Run #184

DAF, sulfamide, dimethylbutylamine and 1,2,3,4-tetrahydronapthalene (in amounts as listed in Tables 7 and 8) were transferred into a 250 mL round-bottomed flask. The flask was placed in a heated oil bath (136° C.) and the mixture agitated while heating at the selected temperature for the selected time (see Table 8). The reaction mixture was cooled to about room temperature and then extracted twice with 1M NaOH (75 mL portions). The aqueous extracts were neutralized using 6M HCl and agitated for 2 hrs to allow crystallization. The crystals were collected by filtration and then dried for about 17 hrs 45 min in a vacuum oven at 52° C. The product was then tested by HPLC analysis.

Run #185–187

DAF, sulfamide, isoquinoline and the chosen solvent (in amounts as listed in Tables 7 and 8) were transferred to a 250 mL round-bottomed flask. The reaction mixture was then placed in an oil bath and agitated while heating at the selected reaction temperature for the selected time (see Table 8). The reaction mixture was cooled to about room temperature and then extracted twice with 1M NaOH (75 mL portions). The aqueous extracts were neutralized with 6M HCl and allowed to stand at room temperature for several days to facilitate crystallization. The crystals were collected by filtration and then dried about 16–18hrs in a vacuum oven at 50° C. The dried product was analyzed by HPLC analysis.

Note: All experimental runs yielded topiramate product except as noted herein. An emulsion was observed to form during the extraction of Experimental Run #187 and although topiramate product was expected, no product was collected. The product collected from Experimental Runs #187, 191, 194 and 197 was expected to be topiramate, but not analyzed.

Tables 7 and 8 below list the run conditions for the experimental procedures described above. Except as noted above, all experimental runs yielded topiramate product.

TABLE 7

| Run# | Base | Base (g) | Solvent | Solvent (mL) |
|---|---|---|---|---|
| 157 | Imidazole | 1.01 | p-Xylene | 15.1 |
| 158 | 4-(Dimethylamino)-pyridine | 1.77 | p-Xylene | 15.2 |
| 159 | 4-(Dimethylamino)-pyridine | 42.08 | o-Xylene | 40 |
| 160 | 4-Picoline | 1.38 | p-Xylene | 15 |
| 161 | 4-Picoline | 42.48 | o-Xylene | 150 |
| 162 | 4-Picoline | 42.92 | Tetrahydro-napthalene | 40 |
| 163 | 4-Picoline | 43.03 | Diphenyl Ether | 40.5 |
| 164 | 2,6-Lutidine | 1.55 | p-Xylene | 15 |
| 165 | Pyridine | 1.15 | p-Xylene | 15 |
| 166 | Pyridine | 14.7 | pyridine | 15 |
| 167 | Pyridine | 1.17 | 1-Methyl-2-pyrrolidinone | 15 |
| 168 | Pyridine | 1.14 | Toluene | 15 |
| 169 | Pyridine | 1.15 | 4-Methyl-2-pentanone | 15 |
| 170 | Pyridine | 1.15 | Benzonitrile | 15 |
| 171 | Pyridine | 1.15 | p-Xylene | 15.1 |
| 172 | Pyridine | 1.17 | Dimethyl-formamide | 15 |
| 173 | Pyridine | 17.29 | mixed xylenes | 300 |
| 174 | Pyridine | 18.23 | Mesitylene | 150 |

TABLE 7-continued

| Run# | Base | Base (g) | Solvent | Solvent (mL) |
|---|---|---|---|---|
| 175 | Pyridine | 18.22 | o-Xylene | 150 |
| 176 | Pyridine | 18.22 | Tetramethylene sulfone | 150 |
| 177 | Pyridine | 18.22 | Biphenyl | 150 g |
| 178 | Pyridine | 18.20 | Tetrahydro-napthalene | 150 |
| 179 | Pyridine | 18.23 | Diphenyl Ether | 151 |
| 180 | Pyridine | 12.17 | 3:1 Diphenyl Ether:Biphenyl | 100.04 g |
| 181 | 4-tert-Butylpyridine | 31.17 | mixed xylenes | 150 |
| 182 | 4-tert-Butylpyridine | — | 4-tert-Butylpyridine | 75 |
| 183 | 4-tert-Butylpyridine | 20.78 | mesitylene | 100 |
| 184 | Dimethylbutylamine | 59.95 | Tetrahydro-napthalene | 40 |
| 185 | isoquinoline | 58.11 | isoquinoline | — |
| 186 | isoquinoline | 20.05 | o-Xylene | 50 |
| 187 | isoquinoline | 59.65 | Diphenyl Ether | 40.5 |
| 188 | Tributylamine | 85.49 | o-Xylene | 40 |
| 189 | Dimethyl-benzylamine | 62.33 | o-Xylene | 40 |
| 190 | Dimethyldodecyl-amine | 98.42 | o-Xylene | 40 |
| 191 | Hexadecylamine | 83.62 | o-Xylene | 40 |
| 192 | Dimethyltetradecyl-amine | 111.22 | o-Xylene | 40 |
| 193 | Dimethylhexadecyl-amine | 124.30 | o-Xylene | 40 |
| 194 | Dimethyloctadecyl-amine | 137.13 | o-Xylene | 40 |
| 195 | morpholine | 30.30 | o-Xylene | 40 |
| 196 | pyrrolidine | 25.74 | o-Xylene | 40 |
| 197 | urea | 20.29 | o-Xylene | 40 |
| 198 | (none) | — | o-Xylene | 40 |

TABLE 8

| Run # | DAF (g) | Sulfamide (g) | Time (min) | Target Temp (C.) |
|---|---|---|---|---|
| 157 | 0.76 | 0.84 | 30 | 115 |
| 158 | 0.74 | 0.84 | 30 | 115 |
| 159 | 30.21 | 22.21 | 30 | 130 |
| 160 | 0.76 | 0.84 | 30 | 115 |
| 161 | 30.07 | 22.34 | 62 | 140 |
| 162 | 30.01 | 22.18 | 62 | 150 |
| 163 | 30.02 | 22.34 | 67 | 140 |
| 164 | 0.75 | 0.84 | 30 | 115 |
| 165 | 0.76 | 0.84 | 30 | 115 |
| 166 | 0.74 | 0.84 | 30 | 115 |
| 167 | 0.73 | 0.83 | 31 | 115 |
| 168 | 0.75 | 0.85 | 30 | 115 |
| 169 | 0.75 | 0.84 | 30 | 115 |
| 170 | 0.76 | 0.85 | 30 | 115 |
| 171 | 0.77 | 0.85 | 30 | 115 |
| 172 | 0.76 | 0.83 | 30 | 115 |
| 173 | 15.02 | 19.46 | 90 | 130 |
| 174 | 15.02 | 11.08 | 60 | 130 |
| 175 | 15.05 | 11.07 | 60 | 130 |
| 176 | 15.01 | 11.08 | 60 | 130 |
| 177 | 15.04 | 11.08 | 60 | 130 |
| 178 | 15.02 | 11.08 | 60 | 130 |
| 179 | 15.03 | 11.07 | 60 | 130 |
| 180 | 10.03 | 7.38 | 60 | 140 |
| 181 | 15.03 | 11.08 | 60 | 130 |
| 182 | 7.49 | 5.53 | 60 | 130 |
| 183 | 10 | 7.38 | 60 | 150 |
| 184 | 29.99 | 22.34 | 60 | 110 |
| 185 | 30.09 | 22.24 | 62 | 140 |
| 186 | 10.04 | 7.38 | 60 | 140 |
| 187 | 30.08 | 22.45 | 57 | 130 |
| 188 | 30.05 | 22.31 | 30 | 130 |

TABLE 8-continued

| Run # | DAF (g) | Sulfamide (g) | Time (min) | Target Temp (C.) |
|---|---|---|---|---|
| 189 | 30.03 | 22.22 | 30 | 140 |
| 190 | 30.17 | 22.26 | 30 | 130 |
| 191 | 30.09 | 22.04 | 30 | 130 |
| 192 | 30.1 | 22.21 | 30 | 130 |
| 193 | 30.11 | 22.28 | 30 | 130 |
| 194 | 30.18 | 22.33 | 30 | 130 |
| 195 | 30.06 | 22.26 | 30 | 130 |
| 196 | 30.01 | 22.26 | 30 | 130 |
| 197 | 30.13 | 22.32 | 30 | 130 |
| 198 | 30.02 | 22.16 | 30 | 130 |

EXAMPLE A5

Topiramate was prepared according to the process of the present invention. Listed below are experimental procedures for the experiments. Tables 9 and 10 which follow list detailed experimental conditions.

Experiment 2:

DAF, sulfamide, pyridine, and o-xylene in amounts as listed in Table 9 below were charged to a 1-liter reactor. The reactor was heated to a jacket temperature of about 155° C. and maintained at that temperature for 30 minutes. The reactor was cooled to 60° C. and distillation was started under vacuum, with distillation continued until there was no remaining liquid to distill. 1M NaOH was added to separate the reaction mixture into layers. The bottom, aqueous layer was drained and transferred to a separatory funnel. 1M NaOH was added to separate the layers further. Again, the lower, aqueous layer was drained and transferred to a clean reactor. 6M HCl was added to neutralize solution to pH 7. The product crystallized, was filtered, and then dried to yield topiramate.

Experiments 3–8, 19–21:

DAF, sulfamide, pyridine, and o-xylene in amounts as listed in Table 9 below were charged to a 1-liter reactor.

The reactor was heated and held at the selected temperature for 4 the selected time (see Table 10), then cooled rapidly to 65° C. Once cooled, vacuum was applied, resulting in the distillation of some amount of organic liquids. The temperature during distillation was maintained between 55° C. and 75° C. After distillation, some amount (0 to 200 milliliters) of NaOH (from strength of 1M to 3.5M) was added to split the reaction mixture into two separable phases, organic on top and aqueous on bottom. The bottom, aqueous layer was drained and transferred to a clean reactor. Acid (6M HCl) was added to neutralize the reaction mixture to pH 7. The product crystallized upon neutralization, was filtered and then dried to yield topiramate.

Experiment 9:

DAF, sulfamide, pyridine, and o-xylene in the amounts as listed in Table 9 below were charged to a 1-liter reactor. The reactor was heated to the selected temperature. The reactor was held at the maximum temperature for the selected amount of time (see Tables 9 and 10) and then cooled rapidly to 65° C. Once cooled, vacuum was applied, resulting in the distillation of someof the organic liquids. The temperature during distillation was maintained between 55° C. and 75° C. After distillation, 3.5M NaOH was added to split the reaction mixture into two separable phases, organic on top and aqueous on bottom. The bottom, aqueous layer was drained and transferred to a clean reactor. The reactor was then spiked with pyridine (40 mL). Acid (6M HCl) was added to neutralize the reaction mixture to about pH 7. The product crystallized upon neutralization and was then filtered and dried to yield topiramate.

Experiments 10, 15–17:

DAF, sulfamide, pyridine, and o-xylene in amounts as listed in Table 9 below were charged to a 1-liter reactor. The reactor was heated to the selected temperature. The reactor was held at the selected temperature for the selected time (see Tables 9 and 10) and then cooled rapidly to 65° C. Once cooled, 3.5M NaOH was added to split the reaction mixture into two separable phases, organic on top and aqueous on bottom. The bottom, aqueous layer was drained and transferred to a clean reactor. Vacuum and heat were applied to distill off aqueous liquid. Acid (6M HCl) was added to neutralize the reaction mixture to about pH 7. If product did not crystallize after neutralization, additional water was added: for Experiment #15 350 mL water was added; for experiments #16 390 mL water was added; for Experiment #17 120 mL water was added. When the product had crystallized, it was filtered and dried to yield topiramate.

Experiment 11:

DAF, sulfamide, pyridine, and o-xylene in amounts as listed in Table 9 below were charged to a 1-liter reactor. The reactor was heated to the selected temperature, held at this temperature for the selected time (see Tables 9 and 10) and then cooled rapidly to 65° C. Once cooled, 3.5M NaOH was added to split the reaction mixture into two separable phases, organic on top and aqueous on bottom. The bottom, aqueous layer was drained and transferred to a clean reactor. Vacuum and heat were applied, resulting in the distillation of some of the aqueous liquid. The reactor was heated to 60° C., and acid (6M HCl) was added to neutralize the reaction mixture to pH 7. The reactor was cooled to 1.5° C. and then water was added until crystals formed. The product crystallized and was then filtered and dried to yield topiramate.

Experiments 12–14:

DAF and sulfamide, in amounts as listed in Table 9 below were charged to a 1-liter reactor. The reactor was heated to the selected temperature. The reactor was held at the selected temperature for the selected time (see Tables 9 and 10) and then cooled rapidly to about room temperature. Once cooled, 3.5M NaOH was added to split the reaction mixture into two separable phases, organic on top and aqueous on bottom. The bottom, aqueous layer was drained and transferred to a clean reactor. Acid (6M HCl) was added to neutralize the reaction mixture to about pH 7. The product crystallized upon neutralization and was then filtered and dried to yield topiramate.

Experiment 18:

DAF, sulfamide, pyridine, and o-xylene in amounts as listed in Table 9 below were charged to a 1-liter reactor. The reactor was heated to the selected temperature. The reactor was held at the selected temperature for the selected time (see Tables 9 and 10) and then cooled rapidly to 65° C. Once cooled, 3.5M NaOH was added to split the reaction mixture into two separable phases, organic on top and aqueous on bottom. The bottom, aqueous layer was drained and transferred to a clean reactor. Vacuum and heat were applied to distill off about half of the aqueous liquid. The remaining aqueous solution was drained and transferred to a beaker. 6M HCl (60 mL) was added to the cleaned reactor. Reaction mixture and additional 6M HCl were dosed into the reactor to maintain about pH 7. Water was added to induce crystallization. The product crystallized and was then filtered and dried to yield topiramate.

Experiment 19:

DAF, sulfamide and pyridine, in amounts as listed in Table 9 below were charged to a 1-liter reactor. The reactor was heated to the selected temperature. The reactor was held at the selected temperature for the selected time (see Tables 9 and 10) and then cooled rapidly. Once cooled to 22° C., 3.5M NaOH was added to split the reaction mixture into separable phases. Three fifths of the aqueous layer was drained and transferred to a clean reactor. Acid (6M HCl) was then added to neutralize the reaction mixture to about pH 7. Water 100 mL was added to the reaction mixture. The product crystallized, and was then filtered and dried to yield topiramate.

TABLE 9

| Run# | DAF (gms) (mmols) | Sulfamide (gms) (mmols) | Pyridine (gms) (mmols) | O-xylene (mL) | Jacket Temp (° C.) |
|---|---|---|---|---|---|
| 2 | 29.97<br>115.17 | 22.26<br>231.63 | 36.50<br>461.44 | 40.0 | 155 |
| 3 | 100.01<br>384.31 | 73.86<br>768.57 | 121.40<br>1534.77 | 134.0 | 145 |
| 4 | 99.98<br>384.20 | 73.85<br>768.47 | 121.78<br>1539.57 | 134.0 | 145 |
| 5 | 100.04<br>384.43 | 78.21<br>813.84 | 121.82<br>1540.08 | 133.0 | 145 |
| 6 | 99.98<br>384.20 | 73.80<br>767.95 | 121.49<br>1535.90 | 132.5 | 145 |
| 7 | 99.99<br>384.24 | 73.93<br>769.30 | 121.66<br>1538.05 | 134.0 | 145 |
| 8 | 99.94<br>384.04 | 72.52<br>754.63 | 121.43<br>1535.15 | 132.0 | 145 |
| 9 | 100.01<br>384.31 | 73.50<br>764.83 | 12.11<br>153.10 | 134.0 | 145 |
| 10 | 100.01<br>384.31 | 73.86<br>768.57 | 121.84<br>1540.33 | 132.0 | 145 |
| 11 | 100.07<br>384.54 | 73.89<br>768.89 | 121.23<br>1532.62 | 132.0 | 145 |
| 12 | 100.01<br>384.31 | 73.87<br>768.68 | 0.00<br>0.00 | 0.0 | 145 |
| 13 | 100.02<br>384.35 | 73.72<br>767.12 | 0.00<br>0.00 | 0.0 | 145 |
| 14 | 100.10<br>384.66 | 73.74<br>767.33 | 0.00<br>0.00 | 0.0 | 145 |
| 15 | 99.97<br>384.16 | 73.79<br>767.85 | 121.81<br>1539.95 | 133.0 | 145 |
| 16 | 100.12<br>384.74 | 73.94<br>769.41 | 121.49<br>1535.90 | 134.0 | 145 |
| 17 | 99.99<br>384.24 | 73.60<br>765.87 | 121.49<br>1535.90 | n/r | n/r |
| 18 | 99.99<br>384.24 | 73.88<br>768.78 | 122.00<br>1542.35 | 135.0 | 145 |
| 19 | 100.04<br>384.43 | 73.45<br>764.31 | 121.74<br>1539.06 | 0.0 | 145 |
| 20 | 100.00<br>384.28 | 73.87<br>768.68 | 121.43<br>1535.15 | 134.0 | n/r |
| 21 | 99.95<br>384.08 | 73.45<br>764.31 | 121.12<br>1531.23 | 132.0 | 145 |

TABLE 10

| Run # | Rxn Time (min) | Rxn Temp. (° C.) |
|---|---|---|
| 2 | 30 | 130–134 |
| 3 | 30 | 130–135 |
| 4 | 45 | 130–136 |
| 5 | 45 | 130–134 |
| 6 | 43 | 130–134 |
| 7 | 45 | 130–134 |
| 8 | 45 | 130–135 |
| 9 | 48 | 130–133 |
| 10 | 45 | 130–134 |
| 11 | 57 | 130–134 |
| 12 | 60 | 130–142 |
| 13 | 45 | 130–143 |
| 14 | 44 | 130–142 |
| 15 | 45 | 130–133 |
| 16 | 45 | 130–134 |
| 17 | 45 | 130–n/r |
| 18 | 45 | 130–134 |
| 19 | 45 | 130–133 |
| 20 | n/r | 130 n/r |
| 21 | 45 | 130 n/r | n/r indicates that no full temperature range or reaction time was recorded.

EXAMPLE A6

Diacetone fructose (DAF) (780 kg; 780 kg, Batch 1 and 2), pyridine (950.6 kg; 950.0 kg) and xylenes (1950 L; 1950 L) were mixed in a tank and the solution was transferred to a reactor with sulfamide (575 kg; 575 kg). The mixture was heated to 128–133° C. via stepwise heating. More specifically, the mixture was heated from 30 to 65° C. in 80 minutes, then from 65 to 95° C. in 60 minutes, followed by heating from 95 to 113° C. in 60 minutes and 113 to 125° C. in 85 minutes. The reactor jacket temperature was raised in 5° C. increments to heat the batch to 128–133° C. over 30 minutes and then held at the temperature for 30 minutes. The reaction mixture was then cooled at a rate of 30° C. per hour to 40° C. To the mixture was then added purified water (1243 L; 1240 L). The mixture was cooled to 20° C. before 50% NaOH (436 kg; 437 kg) solution was added. Organic and aqueous layers (product layers) were separated and the aqueous layer was filtered and transferred to another reactor. The organic layer was discarded. Purified water (1400 L; 1400 L) was added to the aqueous mixture and residual organics (pyridine and xylene) and water were distilled off under vacuum. The distillation was stopped after distilling a known volume (784 L; 784 L). Glacial acetic acid (214.5 kg; 224.4 kg) was added to neutralize the solution to pH 7. The mixture was seeded with topiramate seeds (1.0 kg; 1.0 kg) and was cooled to 0–5° C. to crystallize the crude topiramate. The crude, wet topiramate (730 kg; 803.8 kg wet yield) was centrifuged and collected.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:

1. A process for the preparation of a compound of formula (I)

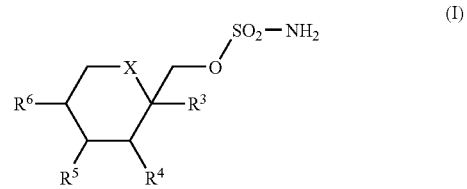

wherein
X is selected from $CH_2$ or O;
$R^3$, $R^4$, $R^5$ and $R^6$ are each independently selected from hydrogen or lower alkyl and, when X is $CH_2$, $R^5$ and $R^6$ may be alkene groups joined to form a benzene ring and, when X is O, $R^3$ and $R^4$ and/or $R^5$ and $R^6$ together may be a methylenedioxy group of the formula:

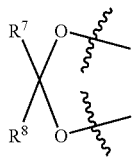

wherein
$R^7$ and $R^8$ are same or different and are hydrogen, lower alkyl or are alkyl and are joined to form a cyclopentyl or cyclohexyl ring;
comprising

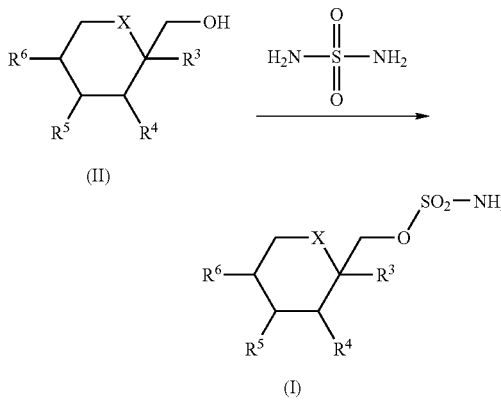

reacting a compound of formula (II) with sulfuryl diamide, at an elevated temperature, in the presence of from 0 to about 10% water, to yield the corresponding compound of formula (I).

2. The process of claim 1, wherein the compound of formula (II) is diacetone fructose.

3. The process of claim 2, wherein the sulfuryl diamide is present in an amount greater than about 0.9 equivalent.

4. The process of claim 3, wherein the sulfuryl diamide is present in an amount equal to about 1.5 to about 3 equivalents.

5. The process of claim 2, wherein the compound of formula (II) is reacted with sulfuryl diamide in the presence of a non-aqueous organic or inorganic base.

6. The process of claim 5, wherein the non-aqueous organic or inorganic base is a tertiary amine base.

7. The process as in claim 6, wherein the tertiary amine base is pyridine.

8. The process of claim 5, wherein the non-aqueous organic or inorganic base is present in an amount greater than about 1 equivalent.

9. The process of claim 8, wherein the non-aqueous organic or inorganic base is present in an amount equal to about 3 to about 5 equivalents.

10. The process of claim 2, wherein the compound of formula (II) is reacted with sulfuryl diamide in an aprotic organic solvent.

11. The process of claim 10, wherein the aprotic organic solvent is a non-aqueous organic base.

12. The process of claim 11, wherein the non-aqueous organic base is pyridine.

13. The process of claim 2, wherein the elevated temperature is in the range of from about 90° C. to about 170° C.

14. The process of claim 13, wherein the elevated temperature is in the range of from about 120° C. to about 140° C.

15. The process of claim 2, wherein the compound of formula (II) is reacted with sulfuryl diamide, in the presence of from 0 to about 3% water.

16. A process for the preparation of a compound of formula (Ia)

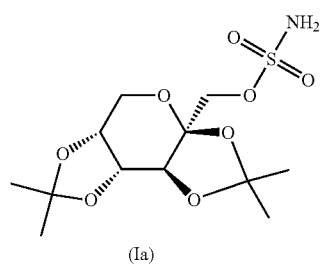

comprising

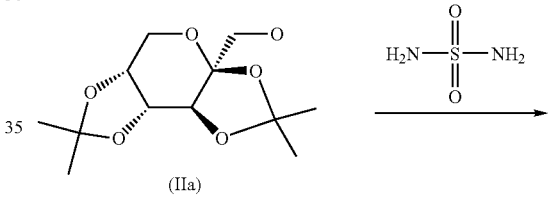

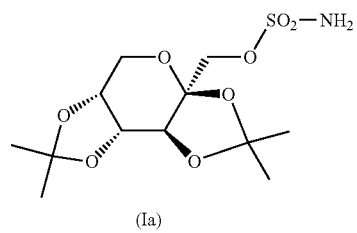

reacting a compound of formula (IIa) with sulfuryl diamide, at an elevated temperature, in the presence of from 0 to about 10% water, to yield the corresponding compound of formula (Ia).

17. The process of claim 16, wherein the sulfuryl diamide is present in an amount greater than about 0.9 equivalents.

18. The process of claim 17, wherein the sulfuryl diamide is present in an amount equal to about 1.5 to about 3 equivalents.

19. The process of claim 16, wherein the compound of formula (IIa) is reacted with sulfuryl diamide in the presence of an non-aqueous organic or inorganic base.

20. The process of claim 19, wherein the non-aqueous organic or inorganic base is a tertiary amine base.

21. The process as in claim 20, wherein the tertiary amine base is pyridine.

22. The process of claim 19, wherein the non-aqueous organic or inorganic base is present in an amount greater than about 1 equivalent.

23. The process of claim 22, wherein the non-aqueous organic or inorganic base is present in an amount equal to about 3 to about 5 equivalents.

24. The process of claim 16, wherein the compound of formula (IIa) is reacted with sulfuryl diamide in an aprotic organic solvent.

25. The process of claim 24 wherein the aprotic organic solvent is a non-aqueous organic base.

26. The process of claim 25, wherein the non-aqueous organic base is pyridine.

27. The process of claim 16, wherein the elevated temperature is in the range of from about 90° C. to about 170° C.

28. The process of claim 27, wherein the elevated temperature is in the range of from about 120° C. to about 140° C.

29. The process of claim 16, wherein the compound of formula (IIa) is reacted with sulfuryl diamide in the presence of from 0 to about 3% water.

* * * * *